United States Patent [19]

Krementsov

[11] Patent Number: 5,658,295

[45] Date of Patent: Aug. 19, 1997

[54] INSTRUMENT FOR MEASURING DILATATION OF CERVIX UTERI

[76] Inventor: Yury Krementsov, 110-11 Queens Blvd. #1J, Forest Hills, N.Y. 11375

[21] Appl. No.: 660,156

[22] Filed: Jun. 3, 1996

[51] Int. Cl.⁶ .................................................. A61B 17/42
[52] U.S. Cl. ........................ 606/119; 128/778; 128/775; 128/774
[58] Field of Search .................. 606/119, 1; 127/774, 127/775, 778

[56] References Cited

U.S. PATENT DOCUMENTS

| | | | |
|---|---|---|---|
| 4,207,902 | 6/1980 | Krementsov | 128/775 |
| 4,226,025 | 10/1980 | Wheeler | 128/724 |
| 4,682,609 | 7/1987 | Parsons | 128/775 |

*Primary Examiner*—Glenn Dawson
*Attorney, Agent, or Firm*—Ilya Zborovsky

[57] ABSTRACT

An instrument for measuring a dilatation of cervix uteri during a first stage of labor, includes two elongated arms pivotally connected with one another in the region of their central portion and having two opposite ends; two loops for passing fingers of a physician and arranged on one end of the arms; a scale arranged on another end of one of the arms and having a plurality of graduation marks which are spaced from one another in a transverse direction. An indicating tip is provided at another end of the other arm and movable relative to the graduation marks when a physician passes his or her fingers through the loops and moves the fingers relative to one another to palpate an edge of an orifice of cervix uteri. A structure for pivotally connecting the arms with one another and a structure for at least temporarily fixing a position of the indicating tip relative to a corresponding graduation mark of the scale when a physician's fingers achieve their final position during determination of dilatation of cervix uteri allows the device to be removed without losing the measurement.

8 Claims, 2 Drawing Sheets

INSTRUMENT FOR MEASURING DILATATION OF CERVIX UTERI

BACKGROUND OF THE INVENTION

The present invention relates to an instrument for measuring dilatation of cervix uteri during the first stage of labor.

It has been known to measure the dilatation of cervix uteri by inserting two fingers into the birth canal to bring them into contact with the edge of the orifice with the dilated cervix uteri and to evaluate the degree of dilatation manually. Such measurements were naturally not accurate. In accordance with my invention disclosed in the U.S. Pat. No. 4,207,902 an instrument was proposed for more accurate determination of the degree of dilatation of cervix uteri. This instrument has two elongated arms, two loops for introducing fingers, a scale and an indicating tip, and means for connecting the arms in the central region, so that fingers can be introduced into the loops and the arms are moved so that the fingers palpate the edge of the orifice while the indicating tip indicates the corresponding graduation mark of the scale. The measurements with this instrument are more accurate. It is believed that it is advisable to further improve the above described instrument.

SUMMARY OF THE INVENTION

Accordingly, it is an object of the present invention to provide an instrument for measuring dilatation of cervix uteri, which is a further improvement of the instrument of this type.

In keeping with these objects and with others which will become apparent hereinafter, one feature of the present invention resides, briefly stated, in an instrument of the above mentioned type which has two arms pivotally connected with one another in their central portion, two loops arranged at one end of the arms so that fingers can extend through the loops to palpate the edge of the orifice, a scale arranged on the opposite end of one arm and a tip arranged on the opposite end of the other arm, so that when the fingers are moved by a physician and the arms are connected to one another the tip points to the corresponding graduating mark of the scale and shows the degree of dilatation of cervix uteri, wherein in accordance to the present invention means are provided for fixing the position of the tip relatively to the scale, so that in the fixed position the physician can still read the graduation mark.

When the instrument is designed in accordance of the present invention, the physician or the nurse cannot make mistakes during measurements since the tip is fixed relative to the scale at least temporarily.

Also, in accordance to this very important feature of the present invention, the whole tool is composed of plastic which facilitates the manufacture of the means for fixing the position of the tip as well as the manufacture of the whole instrument.

The novel features which are considered as characteristic for the present invention are set forth in particular in the appended claims. The invention itself, however, both as to its construction and its method of operation, together with additional objects and advantages thereof, as well as a new method of measuring in accordance with the invention, will be best understood from the following specification and description of specific embodiments when read in connection with the accompanying drawing.

DESCRIPTION OF PREFERRED EMBODIMENTS

Figures 1, 2, 3:
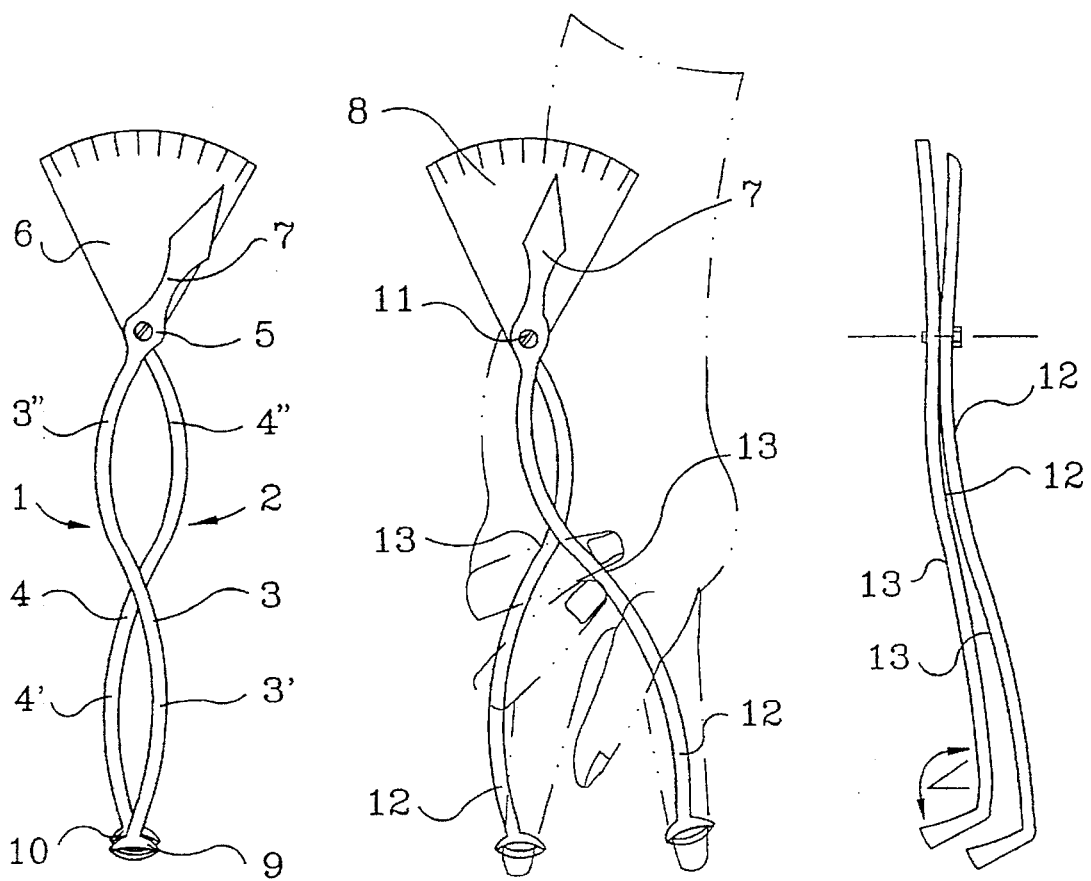
FIG. 1 is a front view of an instrument in accordance with the present invention, in a proximal position of its arms.
FIG. 2 is a view corresponding to the view shown in FIG. 1 but illustrating the instrument in a distal position of its arm.
FIG. 3 is a side view of the instrument in the position shown in FIG. 1.

An inventive instrument for measuring dilatation of cervix uteri has two arms which are identified as a whole by reference numerals 1 and 2. The arm 1 has a measuring portion 3 and an indicating portion 7. Whereas the arm 2 has a measuring portion 4 and an indicating portion 8, The arms 1 and 2 have also central portions 5 and 6, respectively, each located between a respective one of the measuring and indicating portions. The arms 1 and 2 are connected with one another in the region of their central portions 5 and 6 so as to perform a scissors-like movement. The connection may be formed by a screw 11 which is known per se in the art.

The indicating portion 8 of the arm 2 is formed by a sector with rounded edges which is provided with a scale including a plurality of graduation marks. The indicating portion 7 of the arm 1 is formed by an indicating tip adapted to point to the graduation marks of the both a physician and a patient.

As can be seen particularly from FIG. 3, the measuring portions 3 and 4 of the arms are curved in a direction which is transverse to the direction of elongation. The curvature of these portions is so selected as to correspond to the curvature of a physician's palm when his or her fingers are inserted in the birth canal to perform measurements. The arms 1 and 2 have lower surfaces 13 which are flat so as to provide smooth abutment of the instrument against the physician's palm. On the other hand, the arms 1 and 2 are formed by flat members which also have flat upper surfaces so as to prevent injury of a patient by the instrument.

The measuring portions 3 and 4 of the arms have ends which are spaced from the respective central portions 5 and 7 and are provided with loops 9 and 10, respectively. The loop 9 is spaced from the central portions or from the screw 11 by a distance which is greater than the distance by which the loop 10 is spaced from the same. In such a construction, when measuring portions 3 and 4 of the arms in an initial position approach one another, the loops 10 and 9 are located one after the other and they are coaxial with each other. The loops are flattened.

As can be seen particularly from FIG. 1, the measuring portions 3 and 4 have sections 3' and 4' located adjacent to the loops 9 and 10, and sections 3" and 4" located adjacent to the central portions 5 and 6, respectively. The measuring portions 3 and 4 are further so curved that the sections 3' and 3" of the measuring portion 3 are located at opposite sides of a longitudinal axis of the instrument. The same is true with respect to the sections 4' and 4" of the measuring portion 4. On the other hand, the section 3' is located opposite to the section 4', whereas the section 3" is located opposite to the section 4". In such a construction when the arms are moved apart from one another and located in a distal position shown in FIG. 2, the occupy a smaller space in a transverse direction than straight arms would occupy.

A method of measuring in accordance with the present invention is perforated with the use of the above-described instrument in the following manner.

Figure 4:
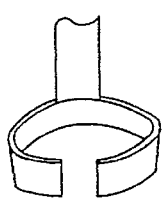
FIG. 4 is a view showing loops which are provided on measuring portions of the instrument, in an enlarged scale.

The arms 1 and 2 are moved toward one another to the initial or proximal position which is shown in FIG. 1. In this position the loops are located one after the other and coaxial with each other. The loops are expandable, for example, they may be constructed of an expandable material, or may be constructed of a springy material and slit as shown in FIG. 4. Preferably, the loops have a diameter equal to substantially 1.2 cm which corresponds to the smallest thickness of a second and third finger of a physician's hand. A synthetic plastic material may be utilized as an expandable material, and metal can be utilized as springy material of the loops.

When the loops 9 and 10 are in the above-mentioned proximal position, the physician puts his or her one finger of hand simultaneously into two loops in the coaxial position of the latter, and introduces the instrument into the birth canal. The finger is so inserted into the loops that it extends outwardly beyond the latter. The thus-extended finger palpates the edge of the orifice of cervix uteri in an initial stage of dilatation. If the one finger and thereby the loops 9 and 10 in the coaxial position contact the edge, the indicating tip 7 will point to the graduation mark corresponding to 1.2 cm.

During further dilatation of cervix uteri, the measuring portions 3 and 4 are moved apart from one another until the two physicians fingers inserted into two spaced loops (FIG. 2) palpate the edge of the dilated cervix uteri, since the fingers extend outwardly beyond the loops. The loops 9 and 10 are brought into contact with the edges by such movement, and the indicating tip 7 points to a respective one of the graduation marks which corresponds to an instant degree of dilatation of cervix uteri. The loops 9 and 10 are conical in correspondence with the conical shape of the second and the hand fingers. Other fingers hold the instrument.

Thus, on the one hand a physician can palpate the edge of the cervix uteri by his or her hand fingers, and, on the other hand, the accurate results appear on the scale of the instrument. Since the loops are expansible, the second and third fingers of various physicians having differing thickness can be inserted into and extend outwardly beyond the loops so as to palpate the edges of the orifice of cervix uteri. It should further be noted that the indicating tip 7 and scale are provided on the upper surfaces of the arms which face away from the physician pal in operational position, whereas the loops extend from the lower surface of the arm in a direction away from the latter and at a certain angle relative to the arms.

In accordance with the present invention, means are provided for fixing the position of the indicating tip 7 relative to the graduation marks of the scale 8, so that when a physician achieves the final position of his or her fingers which corresponds to the measured dilatation, the position of the indicating tip 7 is fixed relative to the corresponding graduating mark.

Figure 5:
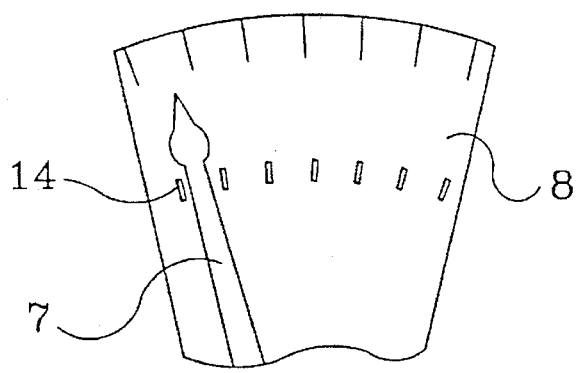
FIG. 5 is a view showing another modification of the scale in accordance with the present invention.

In accordance with one embodiment shown in FIG. 5, the indicating portion or scale 8 on its surface 14 which faces the indicating portion or tip 7 is provided with a plurality of projections extending in a substantially radial direction and spaced from one another in the circumferential direction of the scale, substantially coextensive with the scale but on a smaller radius. The projections 14 are arranged with such distances from one another that when the tip points to the corresponding mark, it extends between two adjacent projections. Therefore the position of the indicating tip with respect to the corresponding graduation mark when the physician achieves the final position of his or her fingers is fixed at least temporarily, the tip does not deviate to the left or to the right on the scale, and the physician can glance on the scale to see the corresponding graduation mark towards which the tip points and to determine the degree of dilatation.

Figure 6:
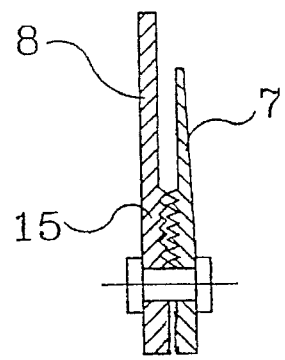
FIG. 6 is a view showing still a further modification of the scale and the tip in accordance to the present invention.
Figure 7:
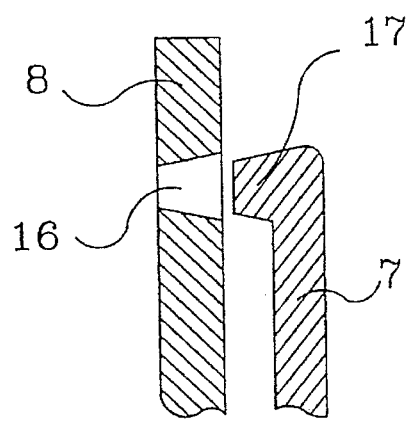
FIG. 7 and 8 are views showing an additional modification of the scale and the tip in accordance with the present invention in an inoperative position and in an operative position correspondingly.
Figure 8:
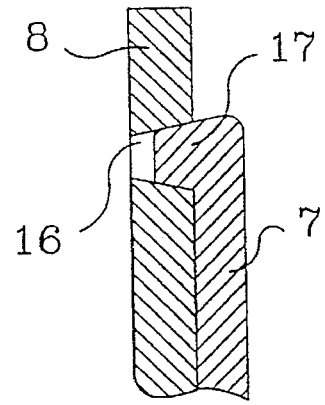

The fixing means of inventive instrument in accordance with another embodiment are shown in FIG. 6. In this embodiment the surfaces of the scale 8 and the indicating tip 7 facing toward one another are provided with a roughening 15. The roughening 15 can be formed in many different ways, for example by forming substantially radially extending grooves on these surfaces, by applying a friction-increasing coating to these surfaces, by providing a plurality of teeth facing one another in a circumferential direction about the pivot axis, by providing circular holes on one surface and circular projections engaging the holes on another surface, etc. In this construction when the fingers of the physician reach their final position which determines the degree of dilatation and the indicating tip 7 points to the corresponding graduation mark of the scale 8, then in view of the roughening the indicating tip also does not deviate easily back and forth along the scale, and the physician can glance on the scale and determine the corresponding graduation mark which shows the degree of dilatation.

In accordance with a further feature of the present invention, the fixing means are formed so that the position of the indicating tip 7 relative to the graduation mark of the scale 8 is fixed even after the physician changes the position of his or her fingers in order to withdraw the instrument from a patient. In this embodiment of the fixing means the scale 8 is provided with a plurality of grooves or holes 16, while the indicating tip 7 is provided with a tooth 17 engageable in the holes 16. Each of the holes 16 and the tooth 17 are conical for the purpose which will be explained herein below. At the same time, the portions of the arms, at least in the area close to the loops, are substantially yieldable in a transverse direction. In this construction when the physician performs measurements, he moves his fingers as before and the indicating tip 7 is positioned against a corresponding graduation mark of the scale 8. When the final position of the physician's fingers is achieved, the physician presses the tooth 17 of the indicating tip 7 into the corresponding hole 16 located opposite to this graduation mark, and in view of the wedge-edge shaped action the tooth 17 is fixed in the hole 16. The physician then withdraws the instrument with his or her fingers. For this purpose he or she moves the fingers toward one another and the portions of the arms located near the loops are somewhat bent inwardly to reduce the size of the instrument for an easy withdrawal. However, the tooth 17 of the indicating tip 7 remains in the hole 16 of the scale 8, thus allowing the physician to read the graduation mark on the scale even when the instrument is removed. It is believed to be clear that the elasticity of the portions of the instrument near the loops has to be selected so that it is not too high in order to allow the correct correspondence between the position of the indicating tip relative to the graduation marks and the position of the physician's fingers inside the patient. At the same time, the flexibility is selected so that it is sufficient to bent these portions of the arms during withdrawal of the instrument. The corresponding portions of the arms as a whole, or even the whole instrument, can be composed of plastic, which is the most preferable embodiment of the present invention.

It will be understood that each of the elements described above may also find a useful application in other types of construction. The invention is not intended to be limited to the details shown, since various modifications may be made without departing from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in particular in the appended claims:

1. An instrument for measuring a dilation of cervix uteri during a first stage of labor, comprising two elongated arms pivotally connected with one another at central portions thereof and having two opposite ends; a loop for passing a finger of a physician arranged on one end of each of the arms; a scale arranged on another end of one of said arms and having a plurality of graduation marks which are spaced from one another in a transverse direction; an indicating tip provided at another end of the other of said arms and movable relative to said graduation marks when a physician passes his or her fingers through said loops and moves said fingers relative to one another to palpate an edge of an orifice of cervix uteri; means for pivotally connecting said arms with one another; means for at least temporarily fixing a position of said indicating tip relative to a corresponding graduation mark of said scale when a physician's fingers achieve a final position during determination of dilatation of cervix uteri, the fixing means including a plurality of projections arranged on said scale so that when said indicating tip points to a corresponding graduation mark of said scale it is located between two adjacent ones of said projections.

2. An instrument as defined in claim 1, wherein said arms, said loops, said scale, said tip, said means for pivotally connecting and said fixing means are composed of a plastic material.

3. An instrument for measuring a dilation of cervix uteri during a first stage of labor, comprising two elongated arms pivotally connected with one another at central portions thereof and having two opposite ends; a loop for passing a finger of a physician arranged on one end of each of the arms; a scale arranged on another end of one of said arms and having a plurality of graduation marks which are spaced from one another in a transverse direction; an indicating tip provided at another end of the other of said arms and movable relative to said graduation marks when a physician passes his or her fingers through said loops and moves said fingers relative to one another to palpate an edge of an orifice of cervix uteri; means for pivotally connecting said arms with one another; means for at least temporarily fixing a position of said indicating tip relative to a corresponding graduation mark of said scale when a physician's fingers achieve a final position during determination of dilatation of cervix uteri, said indicating tip and said scale having surfaces facing toward one another, said fixing means including a roughening provided on at least one of said surfaces.

4. An instrument as defined in claim 3, wherein said fixing means also include a roughening provided on the other of said surfaces.

5. An instrument as defined in claim 3, wherein said arms, said loops, said scale, said tip, said means for pivotally connecting and said fixing means are composed of a plastic material.

6. An instrument for measuring a dilation of cervix uteri during a first stage of labor, comprising two elongated arms pivotally connected with one another at central portions thereof and having two opposite ends; a loop for passing a finger of a physician arranged on one end of each of the arms; a scale arranged on another end of one of said arms and having a plurality of graduation marks which are spaced from one another in a transverse direction; an indicating tip provided at another end of the other of said arms and movable relative to said graduation marks when a physician passes his or her fingers through said loops and moves said fingers relative to one another to palpate an edge of an orifice of cervix uteri; means for pivotally connecting said arms with one another; means for at least temporarily fixing a position of said indicating tip relative to a corresponding graduation mark of said scale when a physician's fingers achieve a final position during determination of dilatation of cervix uteri, said fixing means including a plurality of depressions formed on said scale in correspondence with said graduation marks, and a fixing element formed on said indicating tip and fixedly engageable in a respective one of said depressions, at least one of the arms being yieldable, so that a physician can bend said at least one arm to move his or her fingers toward one another for easy withdrawal of the instrument from a patient, while the fixing element of said indicating tip remains in fixed engagement with the corresponding one of said depressions.

7. An instrument as defined in claim 6, wherein said arms are composed of an elastic plastic material.

8. An instrument as defined in claim 6, wherein said arms, said loops, said scale, said tip, said means for pivotally connecting and said fixing means are composed of a plastic material.

* * * * *